United States Patent [19]
Kubler

[11] Patent Number: 6,152,894
[45] Date of Patent: Nov. 28, 2000

[54] SURGICAL CUTTING INSTRUMENT

[76] Inventor: Harald Kubler, Kotthauser Str. 15, 51647 Gummersbach, Germany

[21] Appl. No.: 09/274,359

[22] Filed: Mar. 23, 1999

[51] Int. Cl.[7] .................................................. A61B 17/20
[52] U.S. Cl. ............................ 604/22; 606/170; 606/185
[58] Field of Search .............................. 604/22; 606/170, 606/185

[56] References Cited

U.S. PATENT DOCUMENTS

| | | |
|---|---|---|
| 3,969,462 | 7/1976 | Stofan . |
| 5,681,277 | 10/1997 | Edwards et al. ........................... 604/22 |
| 5,972,012 | 10/1999 | Ream et al. ............................... 604/22 |

FOREIGN PATENT DOCUMENTS

| | | |
|---|---|---|
| 0729730 | 3/1995 | European Pat. Off. . |
| 7426959 | 11/1974 | Germany . |
| 3277085 | 8/1977 | Germany . |
| 2737014 | 3/1979 | Germany . |
| 3500444 | 7/1989 | Germany . |
| 4329162 | 3/1995 | Germany . |
| 19528440 | 2/1997 | Germany . |

*Primary Examiner*—Michael H. Thaler
*Attorney, Agent, or Firm*—Browdy and Neimark

[57] ABSTRACT

A surgical cutting instrument for introduction into a cutting trocar sleeve possesses an essentially tubular housing shank, which at its distal end able to be introduced into the trocar is provided with an essentially tubular distal section able to be flexed. The distal section possesses at least one cutting means able to be deformed into a working state thereof together with the distal section. At the second, proximal end of the housing shank actuating means are provided with which the cutting means may be moved out of the form as inserted into the working form. The housing shank has a fluid duct, which adjacent to the housing shank distal section is provided with at least one outlet opening. The fluid duct is able to be bent into an arc at the distal section like the cutting means and has a fluid inlet opening at the proximal end thereof.

12 Claims, 4 Drawing Sheets

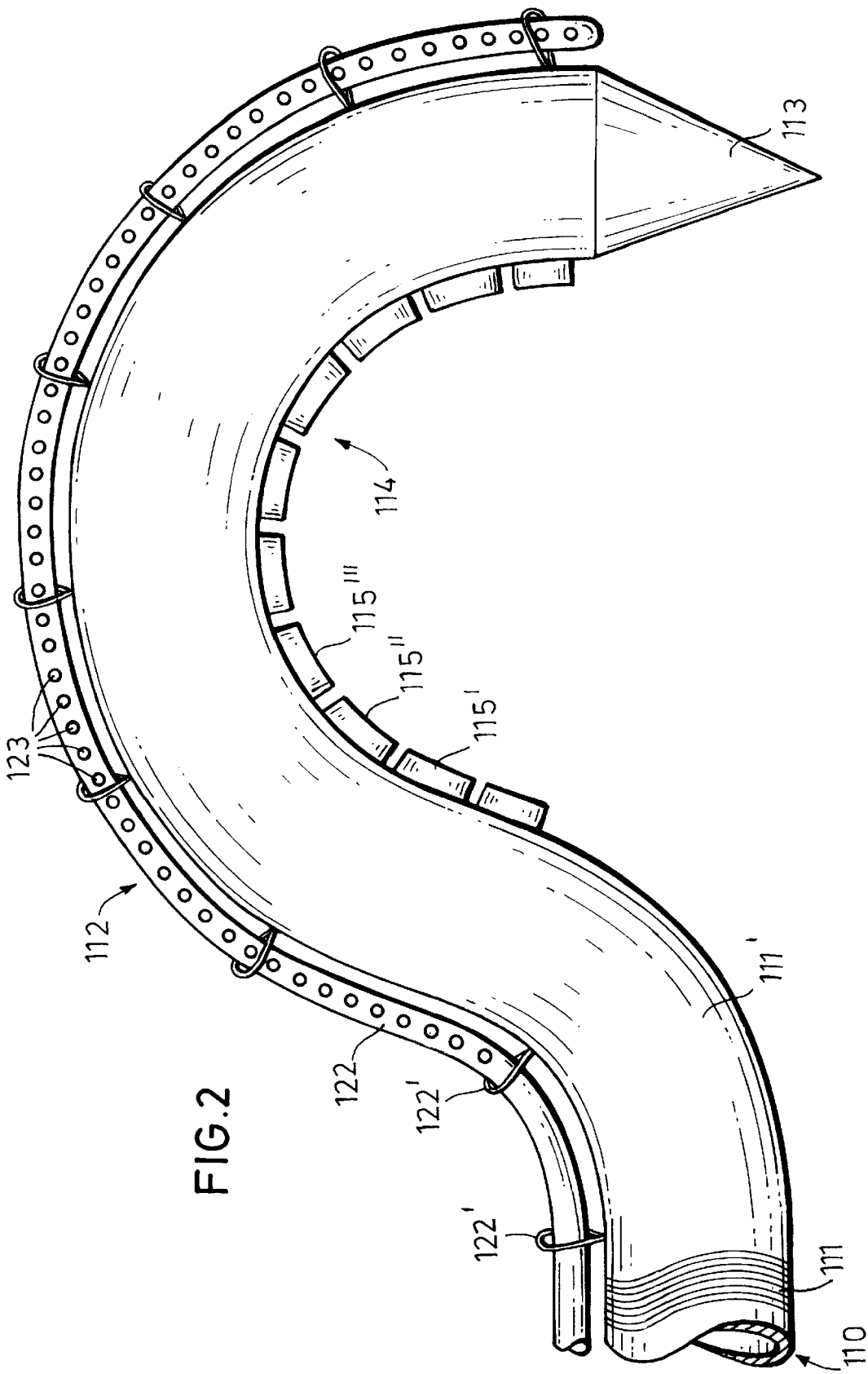

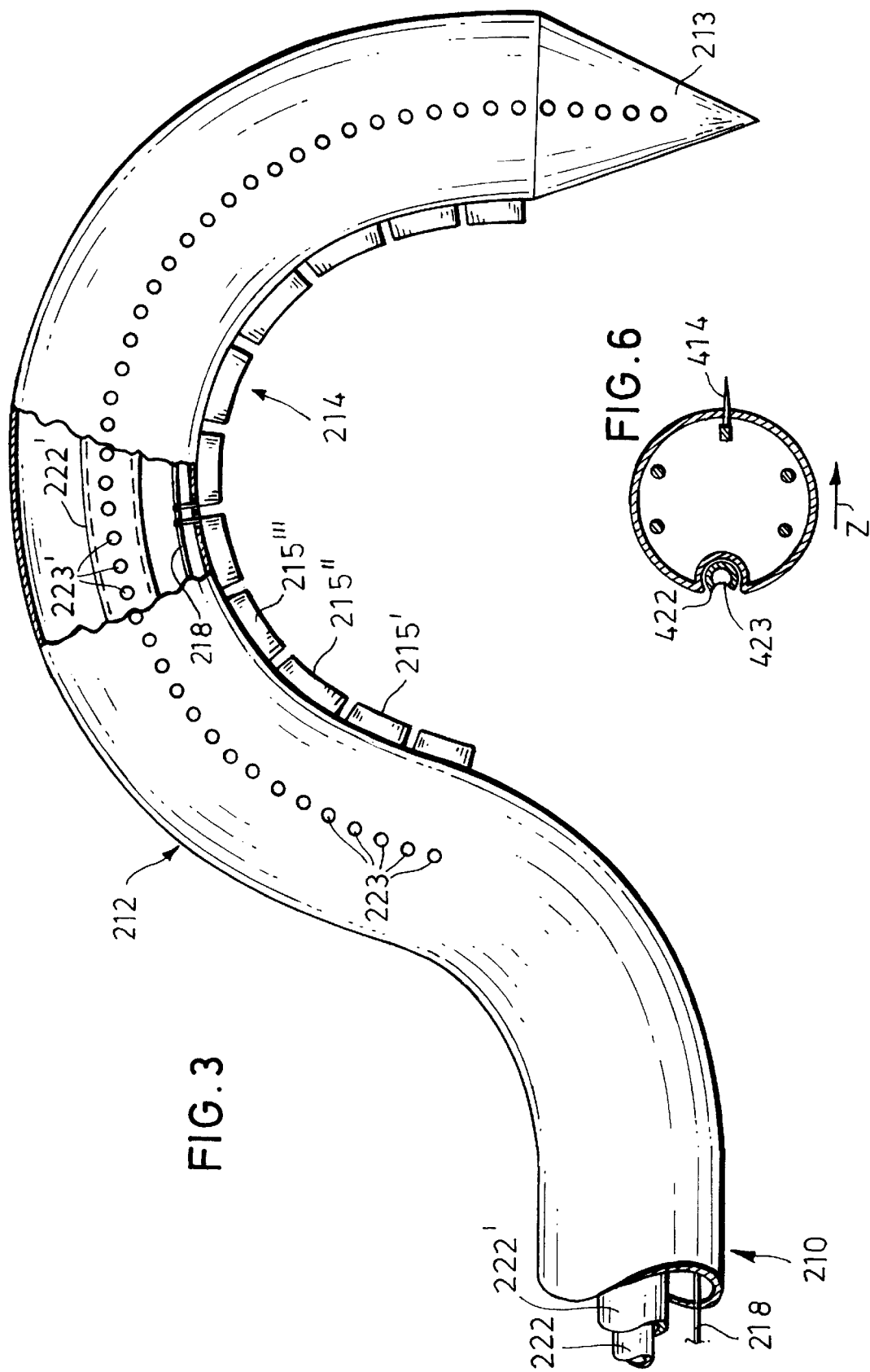

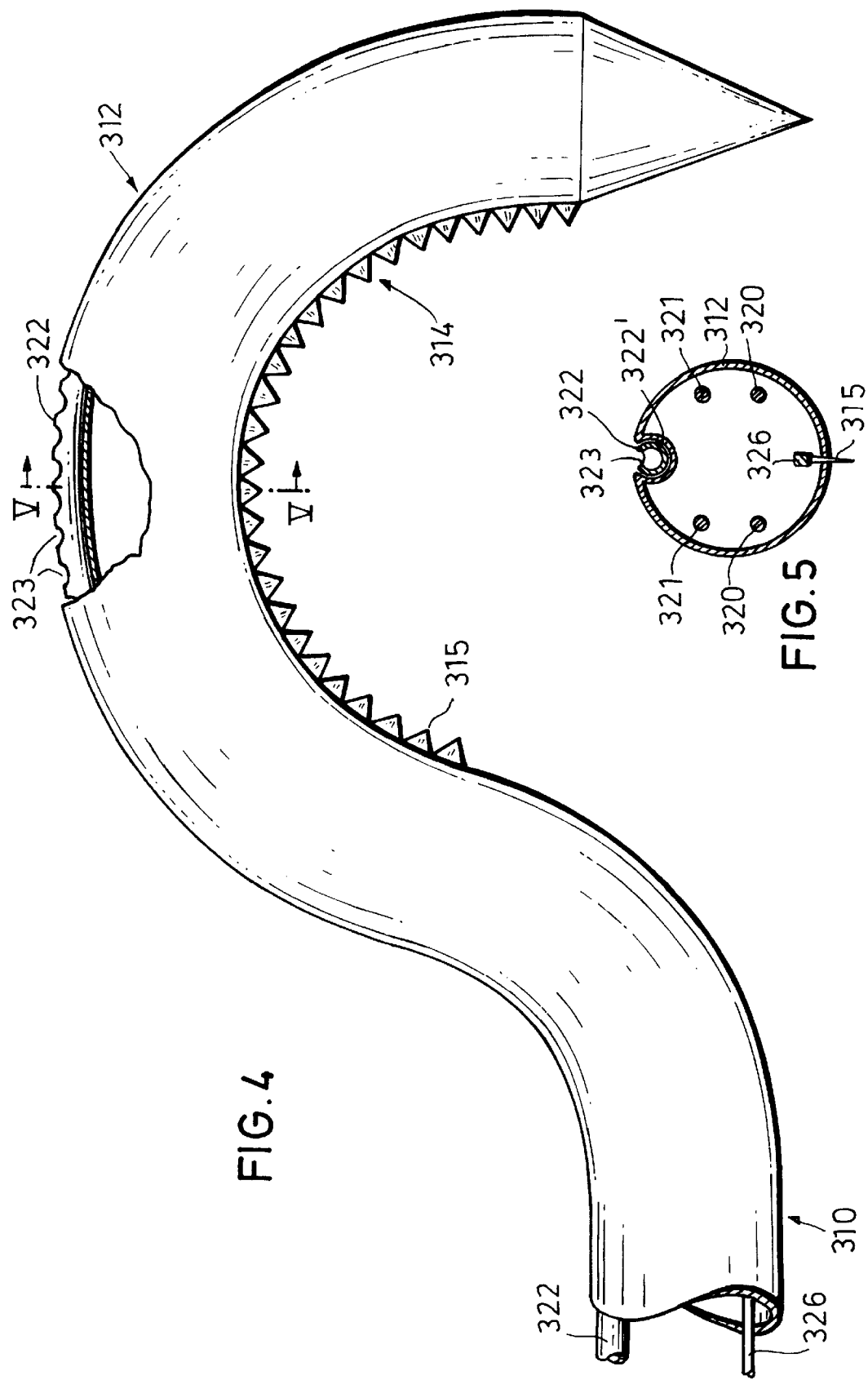

SURGICAL CUTTING INSTRUMENT

BACKGROUND OF THE INVENTION

The invention relates to a surgical cutting instrument for insertion into a cutting trocar sleeve comprising an essentially tubular housing shank, a distal section adapted to be inserted in the trocar sleeve and joined with the housing shank, said distal section having a cutting means and actuating means for the said distal section at a proximal end of the housing shank, the distal section being constituted by a plurality of elements articulatingly joined together, which elements are able to be shifted between a position aligned with the housing shank and an arcuately laterally extended position.

THE PRIOR ART

Such a surgical instrument has been disclosed in the German patent publication 19,528,440 A1. This severing instrument serves to cut off locally limited sections of tissue within the body from the surrounding tissue and to remove same. More particularly when removing metastases in organs of the body, as for instance the liver or lung, a technique is applicable in which the metastases are frozen in situ by a cryoprobe inserted through a trocar and then cut out of the tissue. The frozen metastases as a rule possess a spherical or elliptical shape and the known surgical instrument is employed to cut around same to separate them from the surrounding tissue. For this purpose the known cutting instrument is introduced through the trocar in the interior of the body at the position of the tissue to be removed and during such introduction the distal section with the cutting means is so bent that it has the necessary curvature for cutting around the tissue to be removed. The cutting means is in this case constituted by a piece of wire, which may be heated by being subjected to a high frequency electrical current, or by a flexible blade.

The German patent publication 4,329,162 A1 discloses an endoscope with a moving proximal portion, which possesses a moving section, the shank of the endo cope possessing drive means for shifting the moving section.

SHORT SUMMARY OF THE INVENTION

One object of the invention is to provide a device of the initially described type which is so further developed that it renders possible improved cutting around and possibly removal of cut-free deeply frozen portions of tissue, the discharge of blood or other tissue fluids or particles of tissue into adjacent portion of the body being prevented to a maximum extent while the destruction of tissue is facilitated.

In the present invention the housing shank possesses a fluid duct which functionally adjacent to the distal section of the housing shank is provided with at least one radially outwardly directed outlet opening, such outlet opening being arranged on a laterally externally placed face of the distal section and in the arcuately bent condition of the distal section is trailing behind the cutting means as considered in the direction of rotation, the fluid duct being able to be bent jointly with the cutting means in an arcuate fashion at a position functionally adjacent to the distal section and the fluid duct possesses a fluid inlet opening at the proximal end.

In a manner which is synchronous with the cutting movement, that is to say synchronous with the rotation of the cutting instrument about the axis of the shank of the housing in the bent or deflected condition of the cutting means, the design of the invention renders possible the introduction of a sealant, as for example a wax or a plastic, through the fluid duct and the outlet opening provided into the body at that position, where shortly before the cut was made so that the cut face is sealed off, directly after cutting, with the wax of plastic. It is in this manner that the cut-free, deeply frozen tissue portion is provided with a casing of wax or plastic and so encapsulated. Following this the surgical cutting instrument is withdrawn from the working trocar and simultaneously a hemostatic agent is introduced into the wound.

In accordance with a preferred further development surgical cutting instrument of the invention the outlet section of the fluid duct is provided with a plurality of outlet openings. This means that, more particularly when the openings are small holes in a row, there will be a complete, even discharge of the fluid through the outlet openings and consequently an even encapsulation of the portion of tissue.

In accordance with the invention the outlet opening of the fluid duct in the bent condition of the distal section trails behind the cutting means as considered in the direction of rotation. This means that direct sealing of the cut face is achieved after cutting.

In a further preferred embodiment of the surgical cutting or severing instrument the fluid duct is placed within the periphery of the housing shank and the outlet openings of the fluid duct are constituted by outlet openings in the wall of the housing shank. The complete integration of the fluid duct means that in the case of this embodiment the cutting instrument may be inserted into the body and drawn out of same without any problems.

In order to improve servicing the fluid duct can be placed in a guide tube within the housing shank and the outlet openings in the guide tube are constituted by outlet openings in the guide tube and in the wall of the housing shank. In this embodiment it is possible for the fluid duct to be so designed that a flexible disposable hose may be introduced into the guide tube prior to use, outlet openings in the disposable hose cooperating with the outlet openings in the guide tube and the wall of the housing shank. This design renders it possible to remove the hose, which has become unusable after use owing to the adhesive action of the curing plastic, and therefore to improve cleaning of the surgical cutting instrument and to make it easier to re-use.

In the case of another preferred embodiment the fluid duct is constituted by a piece of hose, which is able to be removably placed in the groove-like recess provided in the surface of the housing shank and extends essentially in the longitudinal direction of the housing shank. In the case of this embodiment the replacement of the flexible hose is simplified, since same merely has to be firmly pressed into the groove and does not have to be threaded into a channel. Furthermore, the outlet openings in the hose housing are simultaneously employed as outlet openings for the fluid without having to provide separate outlet openings in the housing shank, respectively, in its outlet section.

Preferably the fluid duct is provided at its opening with a connection for a pump or a syringe for the introduction under pressure of a fluid into the fluid duct. This connection simplifies the use of the cutting instrument, since the pump or the syringe only has to be connected when the cutting instrument is already introduced into the body, and the measures necessary for cutting around the portion of tissue must be taken. Instead of a pump or a syringe it is naturally possible to employ any other supply device the fluid to be introduced into the body.

Preferably in the arcuately bent condition of the distal section the cutting means is in the face of the distal section which is leading in terms of the direction of rotation. This means that the spherical or elliptical piece of diseased tissue to be cut out may be cut around in the most convenient fashion.

In a particular form of the invention the cutting means possesses at least one movable blade, which with the aid of a drive transmission means, which extends in the interior of the housing shank, is able to be driven from a drive means arranged functionally at the proximal end. This movable blade may comprise a plurality of blade elements arranged like links or two blades placed parallel to one another and able to be moved in relation to each other, it also being possible for the cutting means to be fitted with cutting teeth like those of a saw. Such movably driven cutting means render possible the cutting out of hard portions of tissue. As a drive it is possible to provide a motor for example, which is provided at the proximal end of the cutting instrument, that is to say the outside the body, or same is provided independently of the cutting instrument and is connected with same via a rotary shaft or any other means for the transmission of rotary force.

As an alternative it is possible for the cutting means to comprise at least one stationary blade as well.

The cutting means may also have one or more blades or a wire arranged to be subjected to high frequency current.

Further advantageous developments and convenient forms of the invention will be understood from the following detailed descriptive disclosure of embodiments thereof in conjunction with the accompanying drawings.

LIST OF THE SEVERAL VIEWS OF THE FIGURES

FIG. 2 shows a view of the distal section on a larger scale, of a further cutting means with an externally placed fluid duct.

FIG. 3 shows an alternative embodiment having two integrated fluid ducts.

FIG. 4 shows a still further embodiment of the cutting instrument having motor-driven cutting teeth like those of a saw.

FIG. 5 shows a sectional view taken on the line V—V of FIG. 4.

FIG. 6 is a sectional view of an alternative design.

DETAILED ACCOUNT OF WORKING EMBODIMENTS OF THE INVENTION

Figure 1:
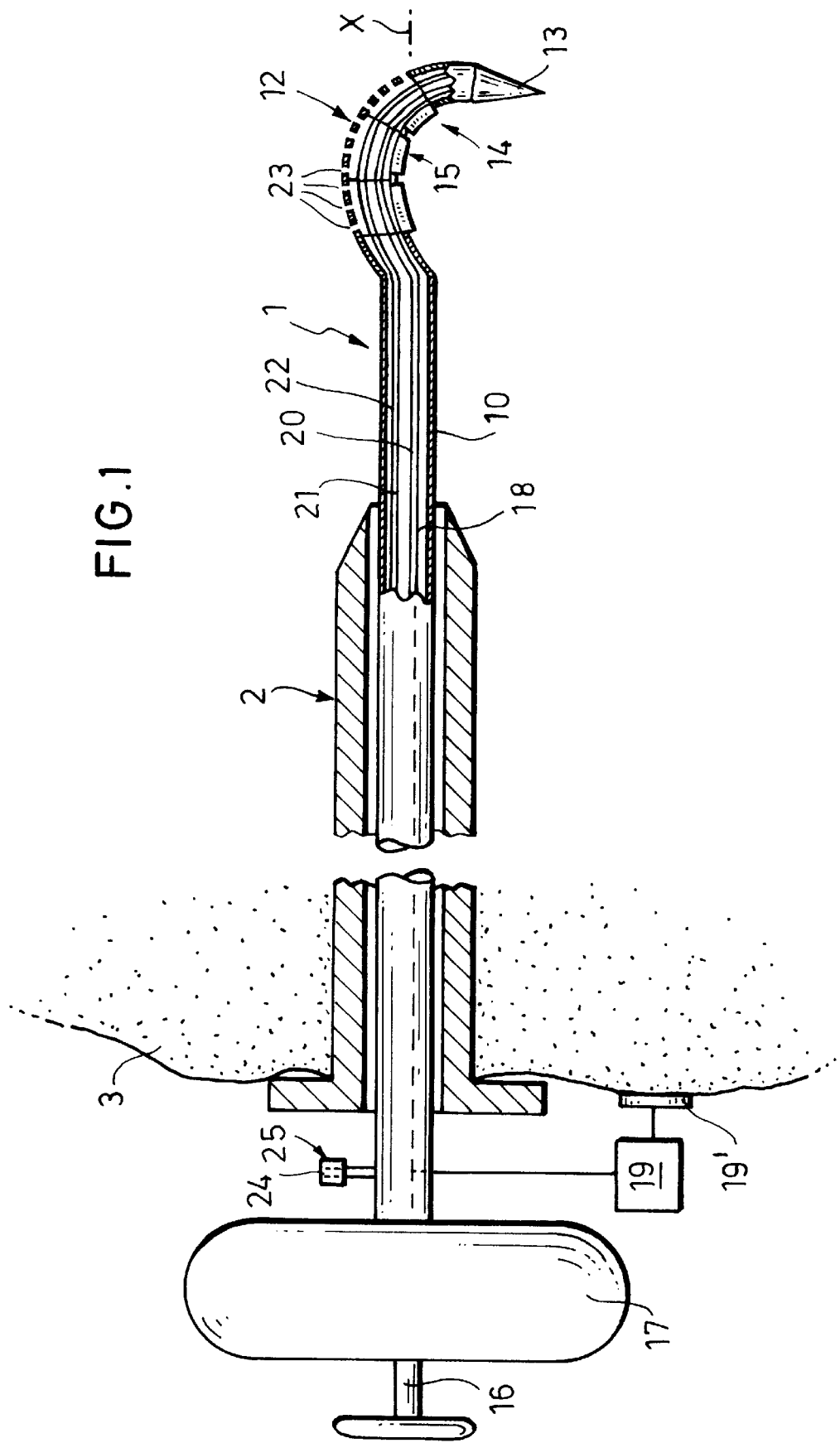
FIG. 1 shows a first embodiment of a surgical cutting instrument in accordance with the invention having high frequency cutting wires and a fluid duct integrated in the housing shank.

FIG. 1 shows a surgical cutting instrument 1, which is inserted into a surgical working trocar 2, which is introduced into a diagrammatically illustrated body 3. The cutting instrument comprises a tubular hollow trocar housing shank 10, whose external diameter (3–12 mm, and preferably 3–5 mm) is so adapted to the inner diameter of the instrument bore in the trocar 2 that the cutting instrument may be introduced without any trouble through the trocar 2 into the body 3 and may be withdrawn from it again.

At its distal end introduced into the body 3 through the trocar 2 the cutting instrument 1 is provided with a tubular distal section 12, whose external diameter is essentially the same as the diameter of the housing shank 10. At its distal end the distal section 12 is provided with a point 13 to facilitate penetration into the body tissues.

The distal section 12 comprises a plurality of articulatingly connected elements 12', 12", 12''', . . . . In the interior of such elements 12', 12", 12''', . . . there extend actuation transmission means designed in the form of wires, of which for the sake of simplification only two drive transmission means 12 and 21 are illustrated. In practice however a plurality of actuation transmission means, as for example four to twelve actuation transmission means in the form of wire cables are provided, which set the degree of curvature of the flexible distal section. The drive transmission means 20 and 21 extend in the interior of the housing shank 10 to the end, which is to the outside of the body, of the housing shank 10, at which same is coupled with a handle part 17 and are there coupled with an actuating means 16.

The actuating means 16 may be thrust by a spring (not illustrated) into a neutral position, in which the tubular distal section 12 of the housing shank 10 is not bent and extends as a straight continuation of the housing shank along the axis X of the housing shank. In this initial state it is possible for the cutting instrument 1 to be introduced through the trocar 2 into the body 3, the point 13 facilitating penetration into the tissue of the body.

If the actuating means 16 are operated, for example by thrusting inward (toward the body), the drive transmission means 20 and 21 will produce the curved shape of the distal section 12 as illustrated in FIG. 1. It is also possible to provide other actuating means employed in the endoscope art.

Furthermore a fluid duct 22 extends along in the housing shank 10 and has a diameter preferably between three and nine millimeters. At least functionally adjacent to the distal section the fluid duct 22 is near the surface of the housing shank 10 and, as shown in FIG. 1, extends at the lateral face which is external in relation to the curvature of the distal section 12. The wall of the distal section 12 is here provided with a plurality of openings 23 spaced out along the length of the distal section 12 to create the connection between the interior of the fluid duct 22 and the external surroundings of the cutting instrument 1.

The fluid duct 22 extends through the housing shank 10 in the longitudinal direction and opens functionally adjacent to the end on the outside of the body, of the housing shank 10 in a connection 25, provided with the fluid inlet opening 24, for a pump or a syringe.

On the side face of the distal section 12 a cutting means 14 is formed, which possesses a wire 15 set at a small distance (about 2 to 4 mm) from the surface of the distal section 12, same being secured to the point of the distal section 12 and being inserted into the housing shank 10 at the end, which is remote from the point 12, in the distal section 12, where the wire 15 merges or is connected with an electrical lead 18. The lead 18 leads to a source 19 of high frequency current, only indicated diagrammatically in the drawing, and is connected with one pole thereof, whereas the other pole is connected with the body 3 via a neutral electrode 19'.

The wire 15 is preferably made of stainless steel, tungsten or a tungsten alloy. The wire can for instance also be coated with a polytetrafluoroethylene (PTFE) layer.

By operation of the actuating means 16 the distal section 12 is bent out of its position aligned with the housing shank 10 in the state of insertion into the curved position represented in FIG. 1 in which it has a essentially semicircular configuration. One rotation of the cutting instrument 1 about the axis X renders possible the cutting out of a substantially spherical portion of tissue or one defined by rotation of an ellipse, by means of the cutting means 14, a sealing material such as liquid wax or liquid plastic being simultaneously introduced as a sealant through the inlet opening 24 into the fluid duct 22, emerging from the outlet openings 23 of the fluid duct 22 functionally adjacent to the curved distal section 12 at the back and encapsulating the cut-out such spherical or elliptical portion of tissue.

FIG. 2 shows an alternative design of the front distal section 112 of a housing shank 110, in the case of which the front distal section 112 is constituted by a flexible tube part, whose wall consists of a helically wound wire 111 and a casing 111', whereas the point 113 is formed by a solid stainless steel tip. For the greater part of its length the housing shank 110 is in the form of a rigid tube and it is only adjacent to point of merging with the distal section 112 that it is constituted by a flexible tube part.

Functionally adjacent to the side face, which is external in terms of the direction of rotation, of the curved distal section 112 a plurality of spaced high frequency cutting wires 115', 115", 115,"' are provided, which are arranged adjacent to each other in the longitudinal direction, same jointly constituting the arcuate cutting edge 114. Preferably 10 to 12 high frequency cutting wires are provided having a diameter of about 0.4 mm.

Functionally adjacent to its radially outer periphery the arcuately curved distal section 112 is externally provided with a flexible hose 122, which in such curvature is furnished with a plurality of small adjacently placed holes constituting outlet openings 123, same being arranged adjacent to each other in the longitudinal direction of the hose. At its free end functionally adjacent to the point 113 the hose 122 is sealed off and at its other end lead along the housing shank 110 to a connection, not illustrated, for a pump or syringe provided at the end, on the outer side of the body, of the housing shank 110. Both the cutting edge 114 and also the length, provided with the outlet openings 123, of the hose 112 extend for an angle of curvature equal to approximately 180. The hose 112 is attached with the aid of clamp-like holding means 122' on the housing shank 110 and, respectively, on the front distal section 112 thereof.

The operation of the deflectable front distal section 112 of the housing shank 110 is performed in the same fashion, and with equivalent means, as is the case with the device illustrated in FIG. 1. In this respect it is possible for the operating elements for the individual actuating to be designed in a manner conventional in the endoscope art with handles of non-conductive material.

The cutting edge 114 and the perforated section of the hose 122 may also be formed on the sides, which face away from each other, of the bent distal section 112 the cutting edge the being on the outer side, facing the reader, of the bent or curved distal section 112 and the perforated section of the hose 112 is then arranged on the side, facing away from the reader, of the curved or bent distal section 112 illustrated in FIG. 2.

The distal section 112 can additionally or as an alternative to the wall of helically wound wire, consist a wall of the a plurality of articulatingly joined rings or links, which are able to be slid and pivoted in relation to one another. The thickness of the individual rings is preferably 0.8 to 2 mm and the distance apart of adjacent rings preferably amounts to 0.6 to 1.5 cm. The individual rings are connected together by means of a sheath-like outer skin of a flexible material (for example plastic or rubber), in which each individual ring is firmly set like the skeleton of a snake.

In lieu of high frequency wires 115', 115", 115''', . . . it is possible for the cutting edge 114 to comprise a plurality of cutting blades arranged in the same fashion as the high frequency wires 115', 115", 115''', . . . .

The high frequency wires 115', 115", 115''', . . . are connected with a supply lead, not illustrated, within the housing shank 112, as is indicated in FIG. 1.

FIG. 3 illustrates a modification of the embodiment of FIG. 2, in the case of which a flexible hose 222 is inserted into a guide tube 222'. The guide tube 222' is rigid in the straight part of the housing shank 210 and in the distal section 212 is made flexible. In the wall of the distal section 210 a plurality of adjacently placed outlet openings 223 is provided distributed out along an angle of curvature of approximately 180, such openings 223 being aligned with corresponding outlet openings 223' in the guide tube 222' and in the hose 222.

In the same manner as in the embodiment of FIG. 2 the cutting edge 214 is provided side with a plurality of high frequency cutting wires 215', 215", 215''', . . . , which in the interior of the distal section 112 are connected with a supply lead 218.

In the embodiment of FIG. 3 the outlet openings 223 and 223' extend as far as a position functionally adjacent to the point 213.

In lieu of the high frequency cutting wires 115', 115", 115''' . . . , which each reach a temperature of 800 to 1,500 C, it is also possible to provide sharp blades, arranged in a row as described in connection with FIG. 2, such blades having a length of approximately 10 to 30 mm.

In lieu of the outlet openings provided in the point 213 it is possible here to have an elongated slot as an outlet opening.

FIG. 4 shows a further alternative design, in the case of which the cutting means 314 is constituted by cutting edge 315 with teeth like those of a saw. The saw-like cutting edge 315 extends essentially for an arc of 180 along the curved distal section 312 of the shank 310. The saw-like cutting edge 315 is mounted so that it can be moved to and fro and is able to be actuated via a drive transmission means 326 from a drive motor arranged outside the body. It is in this manner that the saw-like cutting edge 315 may perform a sawing motion and also cut through a hard piece of tissue.

The saw-like cutting means 314 described here may, independently of the design, claimed in this invention, of a surgical cutting instrument with a fluid duct, also be provided in a surgical cutting instrument not having a fluid duct in accordance with the prior art (for example the German patent publication 19,528,440 A1.

FIG. 4 moreover shows a flexible hose 322 arranged and clamped in a groove-like recess 322' so as to extend along the housing shank 310 and in the distal section 312 extends on the outer side, i. e. on the side remote from the reader, of the distal section 312 in the curved condition thereof. In the curved terminal portion 312 the hose 322 is provided on its top side with outlet openings 323.

The flexible design of the distal section 312 and its drive mechanism are the same as in the embodiment of FIGS. 1 through 3.

Instead of a drive arranged outside the surgical cutting instrument of FIG. 4 for the saw-like cutting edge 315 the drive can be integrated in the housing shank 310 as well.

FIG. 5 shows a cross section taken on the line V—V in FIG. 4. This showing serves to indicate how the hose 322, having openings 323 on its top side, is clamped in the groove 322' in the distal section 312. For this purpose drive wires, in the example four thereof in FIG. 5, 320 and 321 are provided, which serve for operation of the flexible distal section 312.

FIG. 6 shows an alternative embodiment in the same sectional view as in FIG. 5, in which however the cutting means 415 is arranged on the leading face as related to the direction Z of rotation. The outlet openings 423 of the hose 422 are in this embodiment of the invention arranged on the trailing face turned away from the cutting means 414.

What is claimed is:

1. A surgical cutting instrument for insertion into a surgical trocar comprising an essentially tubular housing shaft (110), an end section (112) that is insertable into the trocar and connected to the housing shaft (110) and equipped with a cutter (114), an operating means (120, 121) for the end section (112) positioned at a control end Of the housing shaft (110), wherein the end section (112) is formed by a plurality of elements (112', 112" . . . ) that are connected to one another in an articulated fashion and adjustment means for adjusting the end section from a position coaxial with the housing shaft (110) to an extended curved position, wherein the housing shaft has a fluid duct that is provided with at least one outlet that extends radially outward in a region of the end section, such that the outlet is located laterally on an outer side of the end section (12) and, in the curved extended condition of the end section, is located on a rear behind the cutter in a plane of rotation of the end section, such that the fluid duct in the region of the end section can be bent jointly with the cutter, and the fluid duct has a fluid inlet (24) at the control end.

2. A surgical cutting instrument as set forth in claim 1, wherein the fluid duct (22, 122, 222, 322, 422) has a plurality of outlets (23, 123, 223, 323, 423) in a region of the end section.

3. A surgical cutting instrument as set forth in claim 2, wherein
the fluid duct (22, 222, 322,422) is located within the circumferential contour of the housing shaft, and
that the outlets of the fluid duct (22, 222, 322,422) are formed by outlets in the wall of the housing shaft.

4. A surgical cutting instrument as set for the in claim 3, wherein
the fluid duct (222) is located within a guide tubing (222') within the housing shaft (210), and
the outlet of the fluid duct (222) are formed by joint outlets (223, 223') in the guide tubing and in a wall of the housing shaft (210).

5. A surgical cutting instrument as set forth in claim 4, wherein
the fluid duct (322) is formed by a flexible tubing, which is exchangeably insertable into a groove-like depression (322) that is provided in a surface of the housing shaft (310) and essentially extends in a longitudinal direction of the housing shaft.

6. A surgical cutting instrument as set forth in claim 5 wherein
the fluid duct (22, 122, 222, 322, 422) is provided, in the region of a fluid inlet (24) thereof, with a connection (25) for a pump or a syringe for a pressurized conveying of a fluid into the fluid duct (22, 122, 222, 322, 422).

7. A surgical cutting instrument as set forth in claim 6, wherein
in the curved extended condition of the end section, the cutter (414) is located on a front side of the end section in the plane of rotation of the end section (Z).

8. A surgical cutting instrument as set forth in claim 7 wherein
the cutter (314) is formed by at least one movable blade, which can be moved back and forth via drive transfer means (326) that extend inside the interior of the housing shaft (310) by drive means provided in the region of the control end.

9. A surgical cutting instrument as set forth in claim 8, wherein the cutter is provided with saw-tooth cutting edges (315).

10. A surgical cutting instrument as set forth in claim 8, wherein
the cutter is formed by at least one stationary blade.

11. A surgical cutting instrument as set forth in claim 8, wherein
the cutter is formed by at least one blade or wire that can be charged with a high-frequency voltage.

12. A surgical instrument as set forth in claim 6, wherein
the curvable end section has on a outside thereof, a bendable tubing (122) that forms the fluid duct.

* * * * *